(12) United States Patent
Wiggins

(10) Patent No.: US 10,478,414 B2
(45) Date of Patent: Nov. 19, 2019

(54) NEUROREGENERATION SUPPLEMENT

(71) Applicant: Alicia Marie Wiggins, Woodbury, MN (US)

(72) Inventor: Alicia Marie Wiggins, Woodbury, MN (US)

(*) Notice: Subject to any disclaimer, the term of this patent is extended or adjusted under 35 U.S.C. 154(b) by 0 days.

(21) Appl. No.: 15/944,860

(22) Filed: Apr. 4, 2018

(65) Prior Publication Data

US 2018/0280331 A1 Oct. 4, 2018

Related U.S. Application Data

(60) Provisional application No. 62/481,603, filed on Apr. 4, 2017.

(51) Int. Cl.
| | | |
|---|---|---|
| *A61K 31/40* | (2006.01) | |
| *A61K 31/198* | (2006.01) | |
| *A61K 31/675* | (2006.01) | |
| *A61P 29/00* | (2006.01) | |
| *A61P 25/28* | (2006.01) | |
| *A61K 31/191* | (2006.01) | |

(52) U.S. Cl.
CPC .......... *A61K 31/198* (2013.01); *A61K 31/191* (2013.01); *A61K 31/675* (2013.01); *A61P 25/28* (2018.01); *A61P 29/00* (2018.01)

(58) Field of Classification Search
CPC ..................................................... A61K 31/40
See application file for complete search history.

(56) References Cited

U.S. PATENT DOCUMENTS

| | | | | |
|---|---|---|---|---|
| 5,026,721 A | * | 6/1991 | Dudrick | A61K 31/195 514/396 |
| 2013/0034530 A1 | * | 2/2013 | Fantz | A61K 38/54 424/94.2 |

OTHER PUBLICATIONS

Shir et al. Neurosci Lett, 1998, 240(2): 73-6.*
Soybean Wikipedia, 2015.*
Max-Amino with Vitamin B6 from Country Life, 2013.*
Huang et al., Neurol Res., 2000, 22(2): 160-4.*

* cited by examiner

*Primary Examiner* — Rei Tsang Shiao
(74) *Attorney, Agent, or Firm* — Michael A. Essien; Essien Law Office, PLLC

(57) ABSTRACT

A composition for enhancing neuroregeneration of the sciatic nerve in a mammal is provided that includes medicinally effective amounts of glycine, glutamine, and phenylalanine. In some embodiments, the glutamine can be L-glutamine and the phenylalanine can be D, L-phenylalanine. A method for treating sciatic pain is also included.

7 Claims, No Drawings

NEUROREGENERATION SUPPLEMENT

PRIOR APPLICATION

This Application claims the benefit of U.S. Provisional Application No. 62/481,603, entitled "Neuroregeneration Supplement" filed Apr. 4, 2017 which is hereby incorporated by reference.

BACKGROUND

People who suffer from chronic pains, mental health issues such as stress and depression, addictions, and matters of immune health can attest to the challenges and desperation in getting or obtaining treatment for their ailments without the rigor of suffering with adverse effects of the medicaments that they have to take. It is also an issue of concern that almost all the medicament taken or consumed by these patients present yet again foreign material or abstracts into them. One can presently imagine taking opioids for pain and suffering from diarrhea as an outcome, or becoming addicted to the opioids, just as examples.

In other instances, phytochemicals and other herbal chemistry may present medicaments that come with issues of potency and sourcing. Potency, in that phytochemicals are from sources that may affect the efficacy of the medicament caused by location of the plants as grown, weather, soil, and quality of the raw materials used. Biologics offer some solutions to sufferers and there is recognition that biologics may provide challenges because of the process and the additives that make them usable for their intended purpose or purposes.

Degeneration of the nerves have been shown to cause or exacerbate pain that can have nerve ending challenges or neuropathic links. Drugs, phyto-medicaments, herbals and similarly fabricated medicine used to treat issues of neurodegeneration are typically tied to the adverse effects of such treatment. It is thus reasonable to imagine patients who would rather suffer than take medication that would cause them more challenges than those they already know and manage.

From the foregoing and more, it will be appreciated that what is needed in the art is a formulation that provides some relief to sufferers of neurodegeneration challenges that is devoid of the attendant adverse effects and that are essentially borne out of nonforeign components to the mammal or humans consuming it. Such system is disclosed and claimed herein.

SUMMARY

In one embodiment, the present invention provides a combination of neurobiologics comprising essentially of amino acids, preferably glycine, glutamine and phenylalanine for the neuroregeneration necessary to alleviate ailments associated therewith.

In another embodiment of the present invention, the amino acid composition consists of glycine, L-glutamine and D, L-phenylalanine formulated for the purpose of providing relief to patients of neurodegeneration of the nerves.

The composition of the present invention may preferably include the aforesaid amino acids with additives, such as minerals and vitamins for bioavailability, catalytic and other purposes, wherein such additives and vitamins are selected from Vitamin B6 and magnesium gluconate.

In yet another embodiment of the present invention, the compositions of amino acids are provided in ratios suitable to be consumed by mammals of varying weights and sizes.

DETAILED DESCRIPTION

The present invention provides a composition of amino acids, uniquely formulated for the relief of nerve neurodegeneration challenges. When and where there is an injury to the peripheral nervous system, the nerves, whether proximate or distal segment undergoes degeneration at different rates. In a bid to recover from these degeneration of the nerve endings, there is reasonably some regeneration of the distal segment back to the correct targets. The degeneration of nerve endings is undesired and regeneration is preferred to provide relief for the needed neurotransmission for a healthy being or one recovery from nerve ending injury. The work of neurotransmitters in transmitting nerve impulses from neuron to neuron is typically facilitated by amino acids as building blocks of the mammalian biochemical system. Also, disorders and diseases may affect specific neurotransmitters and the chemistry of particular neurons. This change in chemistry can create dysfunction and death of the neuron, pain and disease. An example of nerve ending problem is sciatica.

Amino acids may preferably be useful to regenerate nerve axon ends for the repair of such peripheral nervous systems since amino acids make up the essential of human beings. Thus, it is practical and reasonable to recognize that amino acids in the body of a human may not present the challenges or adverse effects that have become the bane of other medicaments, whether these are formulated by chemical synthesis or in a combination without regard to the naturally occurring components of the mammal or human. The amino acids of the present invention may generally be classified as neurobiologics—a term which essentially combines allopathic medicine with nutritional supplements to provide medical relief for ailments. Nutritional supplements, such as vitamins have benefits that have been widely acclaimed such as Vitamin B6 for catalytic uses.

In an embodiment of the present invention, the amino acids useful for the regeneration of nerve endings and relief of ailments such as mental illnesses, sciatica and peripheral nerve dysfunction comprise glycine, glutamine and phenylalanine. For bioavailability, a magnesium compound and Vitamin B6 may be included in the formulation of the present invention.

In the present invention, glycine is a preferred amino acid utilized as an inhibitory neurotransmitter. Glycine, ($C_2H_5NO_2$) a simple amino acid is usable to help the human body construct normal DNA and RNA strands needed for proper cell function and formation. Glycine also aids in the prevention of muscle breakdown by boosting the body's creatine level. As an inhibitory neurotransmitter, glycine aids in the relief against seizure activity, hyperactivity, and manic (bipolar) depression.

Glycine research and studies have shown efficacy against sciatica, and for the improvement of memory loss and needed relief for those having a variety of ailments such as sleep-depriving conditions, schizophrenia, Parkinson's disease, Huntington disease, jet lag and overwork. Glycine is associated with creating the neurotransmitter that empowers and causes regeneration of neurons or corresponding neurons in the sciatic nerve.

Another amino acid useful in the present invention is glutamine ($C_5H_{10}N_2O_3$). Glutamine is the most abundant free amino acid in the body and is the amino acid that helps boost the immune system and other essential processes in the body, such as when the body is under stress. When the body is under stress, such as that caused by traumatic injury, severe burns infection, glutamine is usable to provide 'fuel' (nitrogen and carbon), and production of excess glutamine may enhance healing of burns, open sore and injury. It is reasonable to note the added value of glutamine in these condition s to provide needed relief. Glutamine is also useful in dissipating muscle pain that may be due to exertion of muscles and can reduce lactic acid that builds up in the body's stressed muscles. In the present invention, the isomer L-glutamine is preferably used to provide the formulation and relief intended. L-glutamine is obtainable from Pure Bulk of Oregon, USA.

Another component of the amino acid formulation of the present invention includes phenylalanine ($C_9H_{11}NO_2$). Phenylalanine is a known antidepressant, particularly with the L-phenylalanine isomer. The D and L isomers provide varying benefits for Parkinson's disease. For this formulation, the D, L-phenylalanine (DLPA) is preferred as it can be used as a painkiller, especially for chronic pains such as arthritis. DLPA is known to operate by slowing down the enzymes that degrade endorphins produced in the brain. Endorphins provide natural painkiller and mood elevator effects; and DLPA has been shown to increase endorphin concentrations, thus providing additional comfort against chronic aches and pains. Other benefits of DLPA include relief for depression, premenstrual syndrome, and increasing the neurotransmitter dopamine. DLPA may provide relief for chronic or acute or chronic pains such as lower lumbar back pain, joint pains resulting from rheumatoid arthritis, osteoarthritis, and other usage stresses; migraines, severe premenstrual spasms, neuritis, neuralgia, fibromyalgia, and postoperative conditions.

More preferably, the composition of the present invention comprises L-glycine, L-glutamine and D, L-phenylalanine. Given the need to provide a ingestible product, the purity and quality of the composition is paramount. The presented combination may be obtainable in varying measures from and formulated into capsules, caplets, powder or liquid blends using Current Good Manufacturing Practices.

To provide bioavailability of the composition for use as intended, some adjuvants may be added. One typical adjuvant is a magnesium compound which may serve to as an anti-stress mineral further helping in the fighting depression and promoting a healthier cardiovascular system. The magnesium compound usable in the present invention is preferably magnesium gluconate ($MgC_{12}H_{22}O_{14}$), a salt of gluconic acid for the purpose of making amino acid more bioavailable. Other benefits of the magnesium compound include healthier and bones and teeth, preventing calcium deposits, kidney stones and gall stones. Preferably, the magnesium gluconate usable in the present invention may be obtainable from Pure Bulk of Oregon, USA.

To promote catalysis of the amino acid of the present invention, vitamin B6 is preferably included in the formulation. Vitamin B6 enhances the assimilation of protein and aids in the prevention of nervous and skin disorders. In use, excess vitamin B6 is excreted from the body and not stored. Generically, vitamin B6 comprises six compounds namely, pyridoxine, an alcohol; pyridoxal, an aldehyde; pyridoxamine, which contains an amino acid; pyridoxyl-5-phosphate (PLP); and pyridoxamine-5'-phosphate (P5P). Vitamin B6 and other raw materials are obtainable form suppliers such as Pure Bulk of Oregon, USA.

The formulation of the present invention preferably includes L-glycine, L-glutamine, DLPA, and optionally vitamin B6 or magnesium gluconate or combinations thereof.

The present invention provides relief for sciatica and other nerve ending injuries and have, by the relief presented to those taking the supplements, effected a regeneration of the neurons. The mechanics of nerve regeneration is undergoing some scientific refinement and several publications note neurogeneration of the peripheral nervous system nerves unlike the known process that the central nervous system does not generally provide for any regeneration of the nerves that may have been frayed or injured.

Effective amounts of the composition suitable to provide the expected relief for sciatic nerve pain which may be a result of nerve ending irritation or for the neuroregeneration of peripheral nerves may vary from mammal to mammal. In some instance, a preferable effective composition of the present invention may be a daily dose of between about 0.02 and about 240 milligrams per pound of a mammal of interest. Mammals, as referred herein may include dogs, human beings, horses and other living mammals as universally and generally designated. Usable ratios of the present invention preferably comprise between about 40 and 95 percent of amino acids and between about 5 and 60 percent of non-amino acids, more preferably between about 45 and 95 percent of amino acids and between about 5 and 55 percent of non-amino acids, most preferably between about 50 and 90 percent of amino acids and between about 10 and 50 percent of non-amino acids.

A capsule, caplet, tablet, powder, syrup, intravenous (IV) fluid, liquid beverage, transdermal patch, or other delivery options for the composition of the present invention may comprise the components of this disclosure preferably between about 35 and 55 percent of L-glycine; between about 5 and 20 percent of L-glutamine; between about 25 and 40 percent of DLPA (D, L-phenylalanine); between about 9 and 15 percent magnesium gluconate; and between about 1 and 3 percent of Vitamin B6. More preferably, the components may be between about 38 and 50 percent of L-glycine; between about 8 and 18 percent of L-glutamine; between about 30 and 40 percent of DLPA (D, L-phenylalanine); between about 9.5 and 14 percent magnesium gluconate; and between about 1 and 2 percent of Vitamin B6. Most preferably, the component may be between about 40 and 48 percent of L-glycine; between about 10 and 15 percent of L-glutamine; between about 30 and 38 percent of DLPA (D, L-phenylalanine); between about 9 and 13 percent magnesium gluconate; and between about 1 and 2 percent of Vitamin B6.

The composition of the present invention may be manufactured according to standard production practices, using Current Good Manufacturing Practices (CGMPs) now known or later implemented for the production of medicaments, neurtrabiologics, neutraceuticals or related products and processes aimed at maintaining the quality and purity of the products for mammalian and specifically, human consumption. Tablets or related products produced under the aforesaid controls may include, for reasons undisclosed herein, magnesium stearate, sodium ascorbate, ascorbic acid, calcium pantothenate, niacinamide, di-alpha tocopheryl acetate, microcrystalline cellulose, artificial colors and flavors, dextrin, starch, mono-and diglycerides, vitamin A acetate, gelatin, FD&C blue #1, FD&C red #3, artificial colors, thiamin mononitrate, pyridoxine, hydrochloride, citric acid, lactose, sorbic acid, tricalcium phosphate, sodium benzoate, sodium caseinate, methylparaben, potassium sorbate, BHA, BHT, ergocalciferol, or cyanocobalamin added for various purposes. These non-essential adjuvants may be included as production demands for the preservation, availability, appeal, taste or other such attributes without affecting the efficacy or functionality of the composition of the present invention.

Example I

A composition comprising about 1000 mg of L-glycine, 750 mg of D, L-phenylalanine, 300 mg of L-glutamine, 25 mg of Vitamin B6, 300 mg of magnesium gluconate and 400 mcg of Vitamin B12 (methylcobalamin) in a formulation ("Formulation A") was taken by a lady with existing long term neurodegeneration of the sciatic nerve, to address an intense burning sciatic pain due to a fall down a flight of stairs. The pain presentation radiated from the hip down the back of the leg to the foot and was persistent; consistent with sciatic nerve pain or injury. Relief from the sciatic nerve pain ensued within an hour of taking the formulation. Taking the formulation at the instance and within a few days of the injury totally relieved the pain, and the pains returned once the treatment was discontinued. When the treatment was reinstated, the pains was disposed of and after about a week on the formulation, the pain was totally gone and normal functioning returned.

Example II

A retired psychiatrist, aged 52, who has had chronic sciatic pain for over 30 years and recovering form opioid addiction, takes Tylenol for pain, is on no other medications; and is otherwise healthy. He now works as a contractor for the past 8 years and presents with irritation of the sciatic nerves and chronic back pain. A composition of the neuroregeneration supplement comprising "Formulation A" as listed in Example I was taken for 3 weeks. Using an assessment tool, he noted pain and inflammation relief, as well as improved mood from his first day of taking the formulation. He continued use of Formulation A (the neuroregeneration supplement) for 3 more weeks and then discontinued use for a week, at which time his pain and inflammation returned in the same places and moodiness returned. He then reinstituted use of the neuroregeneration supplement and pain was completely gone within a few hours.

Example III

"John," age 21, a production and manufacturing worker, has chronic sciatic pain due to repeated injuries from playing basketball. John is otherwise healthy and uses no medications. He used marijuana and Cannabidiol (CBD) oil for pain without positive outcomes. John also has a sensitivity to Ibuprofen and Tylenol. John used the neuroregeneration supplement (Formulation A) for 3 days and noted pain relief from the first day on the supplement and could return to normal activities after 3 days. John had a repeat presentation of the pain 3 weeks later; he then used the neuroregeneration supplement (Formulation A) for 3 more weeks and was not only relieved of the pain but noted an improved mood and less bowl irritation.

Example IV

"Mary," 41, a retired tennis professional had general body chronic pain and was on Selective serotonin reuptake inhibitors (SSRI) antidepressant, opioid pain medication as needed, sleep medication and Over-the-counter (OTC) remedies that proved unsuccessful in managing her pain. Mary took the neuroregeneration supplement (Formulation A) for 3 weeks, noting improvement in pain with the first dose. Mary also noted improved mood and a return to a more balanced sleep schedule.

Example V

"Robin," 44, a medical secretary, has had chronic back pain for over 10 years; was diagnosed as having Fybromyalgia. Robin has many sensitivities to pharmaceuticals and herbal supplements, took allergy shots weekly and was on SSRI antidepressant, as well as opioid medication for pain. She also needed medication for sleep management. Robin did yoga once or twice per week depending upon her chronic pain level. Robin used the neuroregeneration supplement of the present invention (Formulation A) for 3 weeks, and noted pain and inflammation relief, as well as improved mood beginning from her first day on the supplement. She then used the neuroregeneration supplement for 3 more weeks and then discontinued use for a week, at which time her pain and inflammation returned in the same places and her mood swings. Robin restarted use of the neuroregeneration supplement (Formulation A) and the pain was completely relieved after a few hours. Robin continues use of the neuroregeneration supplement and has reduced her medications while increasing her physical activity.

Example VI

"Vanessa," 35, a nursing assistant, presented with chronic pain from an undiagnosed illness. Vanessa was prescribed SSRI antidepressants and multiple doses of Ibuprofen daily for a few years. Vanessa developed stomach irritation in addition to her chronic pain in her lower back, shoulders, knees, ankles and a plethora of muscle pains. She took the neuroregeneration supplement (Formulation A) for 3 weeks. Vanessa noted pain relief and increased mobility, as well as improved mood from her first day on the supplement. Vanessa continued use of the neuroregeneration supplement for one month with continued improvement in her mobility, a notable improvement in mood and her stomach irritation issues.

Example VII

"Vick," 55, a corporate executive, suffered with chronic sciatic pain for over 35 years and complained of pain radiating down his leg. He also noted foot pain from his sciatic nerves injury. Vick was on an SSRI, sleep medication, a Statin medication, high blood pressure medication, and opioid pain medications for several years as needed. Vick used the neuroregeneration supplement for 3 weeks. Upon assessment, Vick noted pain and inflammation relief, as well as improved mood from his first day. He was especially impressed that the neuroregeneration supplement helped the pain down his leg into his foot, resolving it completely by the third day.

Having thus described the preferred embodiments of the present invention, those of skill in the art will readily appreciate that the teachings found herein may be applied to yet other embodiments within the scope of the claims hereto attached. The complete disclosure of all patents, patent documents, and publications are incorporated herein by reference as if individually incorporated.

What is claimed:

1. A composition for enhancing neuroregeneration of peripheral nerves of a mammal consisting:
   between about 40 and 48 percent of L-glycine;
   between about 10 and 15 percent L-glutamine; and
   between about 30 and 37 percent D, L-phenylalanine of the composition.

2. A composition for enhancing neuroregeneration of the sciatic nerves of a mammal, comprising:
   between about 40 and 48 percent of L-glycine;
   between about 10 and 15 percent L-glutamine; and
   between about 30 and 37 percent D, L-phenylalanine of the composition,
   wherein said composition provides effective relief for sciatic nerve pain without adverse effects.

3. The composition of claim 2, further comprising Vitamin B6 or magnesium gluconate of combinations thereof.

4. The composition of claim 2, further comprising between about 9 and 15 percent of magnesium gluconate or about 1 and 3 percent of Vitamin B6 or combination thereof.

5. A method for providing relief for sciatic nerve injury consisting essentially of:
   providing between about 40 and 48 percent_L-glycine;
   providing between about 10 and 15 percent_L-glutamine; and
   providing between about 30 and 37 percent D, L-phenylalanine in a composition suitable to enhance neuroregenation of sciatic nerves.

6. The method of claim 5, wherein non-essential adjuvants are incorporated.

7. The method of claim 5, wherein the non-essential adjuvants are selected from a group consisting essentially of Vitamin B6, magnesium gluconate, magnesium stearate, sodium ascorbate, ascorbic acid, calcium pantothenate, niacinamide, di-alpha tocopheryl acetate, microcrystalline cellulose, artificial colors and flavors, dextrin, starch, mono- and diglycerides, vitamin A acetate, gelatin, FD&C blue #1, FD&C red #3, artificial colors, thiamin mononitrate, pyridoxine, hydrochloride, citric acid, lactose, sorbic acid, tricalcium phosphate, sodium benzoate, sodium caseinate, methylparaben, potassium sorbate, BHA, BHT, ergocalciferol, cyanocobalamin or combinations thereof.

* * * * *